United States Patent
Jones et al.

(10) Patent No.: US 7,195,648 B2
(45) Date of Patent: Mar. 27, 2007

(54) INTRAVASCULAR STENT DEVICE

(75) Inventors: Donald K. Jones, Lauderhill, FL (US); Vladimir Mitelberg, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 122 days.

(21) Appl. No.: 10/425,380

(22) Filed: Apr. 29, 2003

(65) Prior Publication Data
US 2003/0216807 A1   Nov. 20, 2003

Related U.S. Application Data

(60) Provisional application No. 60/381,163, filed on May 16, 2002.

(51) Int. Cl.
*A61F 2/06* (2006.01)
*A61M 29/00* (2006.01)

(52) U.S. Cl. .................. 623/116; 623/1.2; 606/200

(58) Field of Classification Search .............. 623/1.11, 623/1.12, 1.13, 1.14, 1.15, 1.16, 1.17, 1.18, 623/1.19, 1.2, 1.21, 1.22, 23.7; 606/200
See application file for complete search history.

(56) References Cited

U.S. PATENT DOCUMENTS

| | | | |
|---|---|---|---|
| 4,443,498 A | 4/1984 | Shinno |
| 4,512,338 A | 4/1985 | Balko et al. |
| 4,665,906 A | 5/1987 | Jervis |
| 4,733,665 A | 3/1988 | Palmaz |
| 4,739,762 A | 4/1988 | Palmaz |
| 4,739,768 A | 4/1988 | Engelson |
| 4,776,337 A | 10/1988 | Palmaz |
| 4,796,629 A | 1/1989 | Grayzel |
| 4,878,906 A | 11/1989 | Lindemann et al. |
| 4,994,069 A | 2/1991 | Ritchart et al. |
| 4,994,071 A | 2/1991 | MacGregor |
| 5,102,417 A | 4/1992 | Palmaz |
| 5,108,407 A | 4/1992 | Geremia et al. |
| 5,122,136 A | 6/1992 | Guglielmi et al. |
| 5,195,970 A | 3/1993 | Gahara |
| 5,226,887 A | 7/1993 | Farr et al. |
| 5,226,911 A | 7/1993 | Chee et al. |
| 5,261,916 A | 11/1993 | Engelson |
| 5,288,711 A | 2/1994 | Mitchell et al. |
| 5,316,023 A | 5/1994 | Palmaz et al. |

(Continued)

FOREIGN PATENT DOCUMENTS

EP   0 664 104 B1   7/1995

(Continued)

OTHER PUBLICATIONS

U.S. Appl. No. 10/163,248, Mitelberg et al.

(Continued)

*Primary Examiner*—Corrine McDermott
*Assistant Examiner*—Thomas J. Sweet
(74) *Attorney, Agent, or Firm*—Henry W. Collins

(57) ABSTRACT

Disclosed is a very small diameter intravascular stent, or aneurysm cover, which may be used to occlude, or partially occlude, an aneurysm in the human brain. The stent is comprised of a thin-walled skeletal tubular member formed of interconnected sinusoidal members to thereby form a pattern of cells along the skeletal tubular member. The stent also includes anchor members, which are comprised of a longitudinal leg member having a radiopaque coil disposed about the leg member, which serve to retain the stent during delivery of the stent.

26 Claims, 4 Drawing Sheets

U.S. PATENT DOCUMENTS

| | | | |
|---|---|---|---|
| 5,342,348 A | 8/1994 | Kaplan | |
| 5,354,294 A | 10/1994 | Chou | |
| 5,354,295 A | 10/1994 | Guglielmi et al. | |
| 5,360,443 A | 11/1994 | Barone et al. | |
| 5,378,239 A | 1/1995 | Termin et al. | |
| 5,514,176 A | 5/1996 | Bosley, Jr. | |
| 5,516,781 A | 5/1996 | Morris et al. | |
| 5,522,836 A | 6/1996 | Palermo | |
| 5,522,880 A | 6/1996 | Barone et al. | |
| 5,540,712 A * | 7/1996 | Kleshinski et al. | 623/1.19 |
| 5,551,444 A * | 9/1996 | Finlayson | 600/585 |
| 5,551,954 A | 9/1996 | Buscemi et al. | |
| 5,563,146 A | 10/1996 | Morris et al. | |
| 5,565,036 A | 10/1996 | Westendorp et al. | |
| 5,569,245 A | 10/1996 | Guglielmi et al. | |
| 5,571,170 A | 11/1996 | Palmaz et al. | |
| 5,571,171 A | 11/1996 | Barone et al. | |
| 5,578,071 A | 11/1996 | Parodi | |
| 5,578,072 A | 11/1996 | Barone et al. | |
| 5,591,195 A | 1/1997 | Taheri et al. | |
| 5,607,466 A | 3/1997 | Imbert et al. | |
| 5,609,628 A | 3/1997 | Keranen | |
| 5,646,160 A | 7/1997 | Morris et al. | |
| 5,656,023 A | 8/1997 | Caprio, Jr. et al. | |
| 5,656,036 A | 8/1997 | Palmaz | |
| 5,665,728 A | 9/1997 | Morris et al. | |
| 5,683,453 A | 11/1997 | Palmaz | |
| 5,725,548 A * | 3/1998 | Jayaraman | 623/1.15 |
| 5,725,572 A | 3/1998 | Lam et al. | |
| 5,735,893 A | 4/1998 | Lau et al. | |
| 5,741,327 A | 4/1998 | Frantzen | |
| 5,772,668 A | 6/1998 | Summers et al. | |
| 5,800,520 A | 9/1998 | Fogarty et al. | |
| 5,807,404 A | 9/1998 | Richter | |
| 5,810,872 A | 9/1998 | Kanesaka | |
| 5,827,321 A | 10/1998 | Roubin et al. | |
| 5,855,600 A | 1/1999 | Alt | |
| 5,861,027 A * | 1/1999 | Trapp | 623/1.15 |
| 5,931,867 A | 8/1999 | Haindl | |
| 5,980,514 A | 11/1999 | Kupiecki et al. | |
| 5,993,482 A * | 11/1999 | Chuter | 623/1.15 |
| 6,004,347 A | 12/1999 | McNamara et al. | |
| 6,042,597 A | 3/2000 | Kveen et al. | |
| 6,083,257 A | 7/2000 | Taylor et al. | |
| 6,096,034 A | 8/2000 | Kupiecki et al. | |
| 6,106,548 A | 8/2000 | Roubin et al. | |
| 6,117,165 A | 9/2000 | Becker | |
| 6,152,957 A | 11/2000 | Jang | |
| 6,168,592 B1 | 1/2001 | Kupiecki et al. | |
| 6,179,868 B1 | 1/2001 | Burpee et al. | |
| 6,193,747 B1 | 2/2001 | von Oepen | |
| 6,214,025 B1 * | 4/2001 | Thistle et al. | 606/200 |
| 6,231,581 B1 * | 5/2001 | Shank et al. | 606/157 |
| 6,254,612 B1 | 7/2001 | Hieshima | |
| 6,261,319 B1 | 7/2001 | Kveen et al. | |
| 6,267,783 B1 | 7/2001 | Letendre et al. | |
| 6,273,900 B1 * | 8/2001 | Nott et al. | 606/200 |
| 6,287,366 B1 | 9/2001 | Derive et al. | |
| 6,336,938 B1 * | 1/2002 | Kavteladze et al. | 623/1.15 |
| 6,344,041 B1 | 2/2002 | Kupiecki et al. | |
| 6,361,558 B1 | 3/2002 | Hieshima et al. | |
| 6,565,036 B1 | 5/2003 | Palathingal et al. | |
| 6,673,106 B2 | 1/2004 | Mitelberg et al. | |
| 6,991,647 B2 * | 1/2006 | Jadhav | 623/1.2 |
| 2002/0107562 A1 * | 8/2002 | Hart et al. | 623/1.15 |
| 2003/0004567 A1 | 1/2003 | Boyle et al. | |
| 2003/0149475 A1 * | 8/2003 | Hyodoh et al. | 623/1.19 |
| 2004/0044399 A1 * | 3/2004 | Ventura | 623/1.16 |
| 2004/0068314 A1 | 4/2004 | Jones et al. | |
| 2004/0254630 A1 * | 12/2004 | Yang | 623/1.15 |

FOREIGN PATENT DOCUMENTS

| | | |
|---|---|---|
| EP | 0 547 530 B1 | 9/1996 |
| EP | 1 000 590 A1 | 5/2000 |
| EP | 1 042 997 A1 | 10/2000 |
| EP | 1 157 673 A2 | 11/2001 |
| EP | 1266639 A2 | 12/2002 |
| WO | WO 97/25000 | 7/1997 |
| WO | WO 97/26840 | 7/1997 |
| WO | WO 98/32412 | 7/1998 |
| WO | WO 02/054980 A2 | 7/2002 |

OTHER PUBLICATIONS

U.S. Appl. No. 10/743,510, Mitelberg et al.
European Search Report EP 03 25 2992.7 dated Sep. 9, 2003.

* cited by examiner

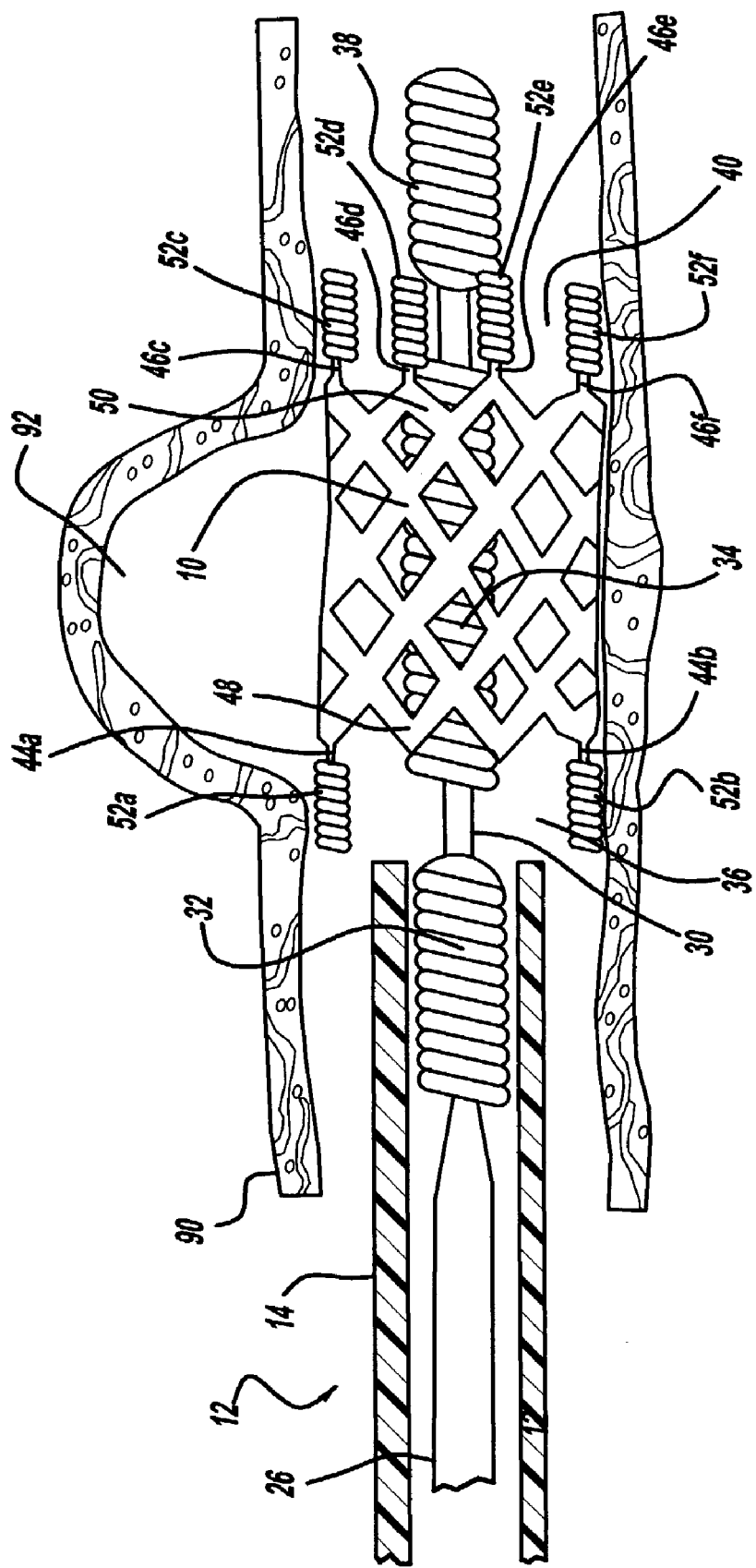

INTRAVASCULAR STENT DEVICE

This patent application claims the benefit of provisional patent application Ser. No. 60/381,163 filed on May 16, 2002.

BACKGROUND OF THE INVENTION

1. Field of the Invention

This invention relates to intravascular devices for implantation within a vessel of the body, and more particularly to a stent device which may be used in the treatment of blood vessel disorders. More specifically, the stent device may take the form of an aneurysm cover to be used in the treatment of aneurysms which occur within the brain.

2. Description of the Prior Art

On a worldwide basis, nearly one million balloon angioplasties are performed annually to treat vascular disease, including blood vessels clogged or narrowed by a lesion or stenosis. The objective of this procedure is to increase the inner diameter or cross-sectional area of the vessel passage, or lumen, through which blood flows. Another serious vascular defect is an area of weakened vessel wall that causes a bulge, or bubble, to protrude out in a radial direction from the vessel. This type of defect is called an aneurysm. If untreated, the aneurysm may continue expanding until it bursts thereby causing hemorrhaging from the vessel.

In an effort to prevent restenosis or to treat an aneurysm without requiring surgery, short flexible cylinders or scaffolds, made of metal or polymers, are often placed into a vessel to maintain or improve blood flow. Referred to as stents, various types of these devices are widely used for reinforcing diseased blood vessels, for opening occluded blood vessels, or to serve as an aneurysm cover to cover the neck of an aneurysm and relieve the pressure within the aneurysm. Some stents are expanded to the proper size by inflating a balloon catheter, referred to as "balloon expandable" stents, while others are designed to elastically expand in a self-expanding manner.

Balloon expandable stents and self-expanding stents are crimped to a small diameter and delivered within a blood vessel using a catheter-based delivery system. When positioned at a desired site within a vessel, these devices are expanded by a balloon, or allowed to self-expand, to the desired diameter. In order to serve as an aneurysm cover, the stent is expanded at a location within the blood vessel adjacent the aneurysm to thereby provide a skeletal cover across the neck of the aneurysm.

One such stent, or aneurysm cover, for the treatment of abdominal aortic aneurysms, is disclosed in U.S. Pat. No. 6,267,783, entitled "Stent Which is Easily Recaptured and Repositioned Within the Body." This patent discloses a self-expanding stent which may be used in the treatment of aortic aneurysms. This device may be easily recaptured after placement and repositioned to a new position within the vessel.

Another stent device used for the treatment of aneurysms is disclosed in U.S. Pat. No. 6,361,558 to Grant Hieshima, et al., entitled "Stent Aneurysm Treatment System and Method." This patent discloses vasculature stents of various configurations which may be used as aneurysm covers for occluding, or partially occluding, aneurysms located at various positions along the blood vessels.

SUMMARY OF THE INVENTION

In accordance with one aspect of the present invention, there is provided a self-expanding stent, or aneurysm cover, which includes a small diameter, thin-walled, skeletal tubular member. The wall of the skeletal tubular member includes a plurality of cells formed by a plurality of interconnected sinusoidal members. The sinusoidal members are generally parallel to the longitudinal axis of the skeletal tubular member and are generally parallel to each other. Each sinusoidal member has a plurality of positive and negative peaks. The positive peaks of each sinusoidal member are connected to the negative peaks of an adjacent sinusoidal member so as to form a repeating cell pattern along skeletal tubular member.

In accordance with another aspect of the present invention, the self-expanding stent, or aneurysm cover, includes a plurality of junctions formed at the distal and proximal ends of the skeletal tubular member. Each junction occurs at a location where a positive peak of a sinusoidal member is connected to a negative peak of an adjacent sinusoidal member. Preferably, a longitudinal leg member extends from four of the junctions at the distal end of the skeletal tubular member and from two of the junctions at the proximal end of the skeletal tubular member. Each of the longitudinal leg members extends in a direction parallel to the longitudinal axis of the skeletal tubular member. Each of the longitudinal leg members also includes a helically wound radiopaque coil disposed about the longitudinal leg member.

In accordance with yet another aspect of the present invention, there is provided a self-expanding stent, or aneurysm cover, which takes the form of a small diameter, thin-walled, skeletal tubular member. The wall of the skeletal tubular member comprises a plurality of cells formed by a plurality of interconnected sinusoidal members. The interconnected sinusoidal members are generally parallel to the longitudinal axis of the skeletal tubular member and are generally parallel to each other. Each sinusoidal member has a plurality of positive and negative peaks. The positive peaks of each sinusoidal member are directly connected to the negative peaks of an adjacent sinusoidal member so as to form a repeating cell pattern along the skeletal tubular member. The stent also includes a plurality of junctions formed at the distal and proximal ends of the skeletal tubular member. Each junction occurs at a location where a positive peak of a sinusoidal member is directly connected to a negative peak of an adjacent sinusoidal member. Longitudinal leg members extend from four of the junctions at the distal end of the skeletal tubular member and from two of the junctions at the proximal end of the skeletal tubular member. Each of the longitudinal leg members extends in a direction parallel to the longitudinal axis of the skeletal tubular member. A helically wound radiopaque coil is disposed about each longitudinal leg member and serves as a radiopaque marker for the stent.

DESCRIPTION OF THE PREFERRED EMBODIMENT

Figure 1:
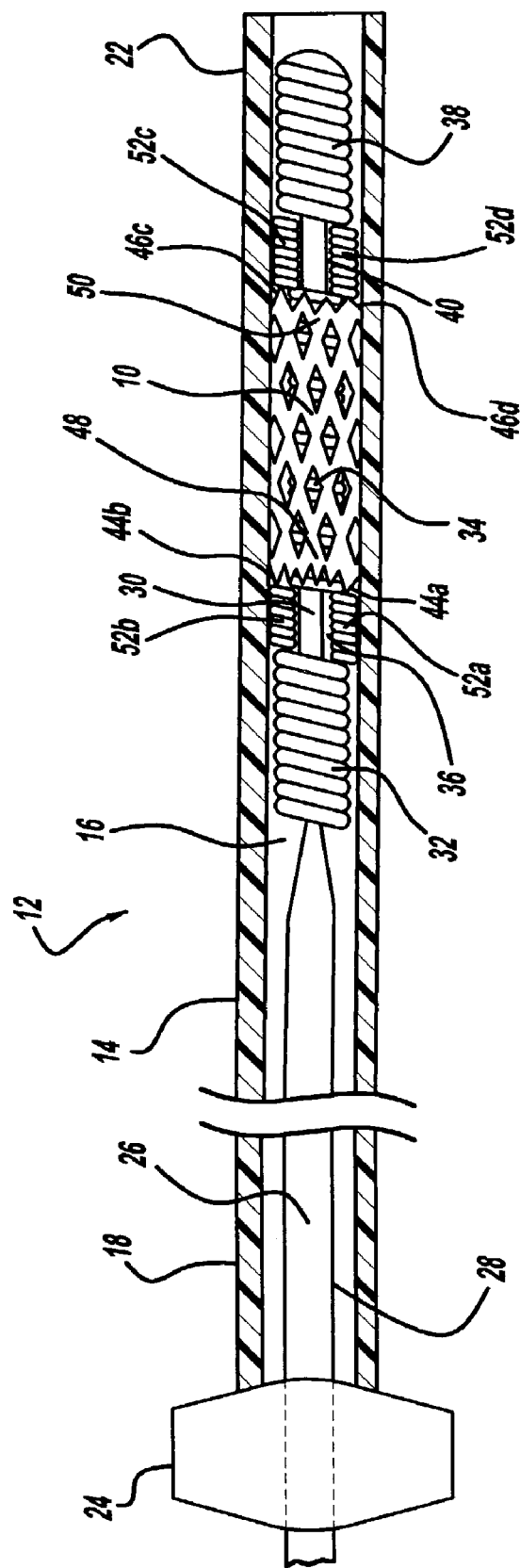
FIG. 1 is an enlarged partial sectional view of an expandable intravascular stent, or aneurysm cover, mounted within a stent delivery system.

FIG. 1 illustrates an expandable intravascular stent 10, or aneurysm cover, and delivery system 12. The delivery system 12 includes a deployment catheter 14 which is an elongated tube having a lumen 16. The lumen 16 of the deployment catheter 14 has a diameter in the range of 0.010 inches to 0.25 inches, with a preferred diameter of approximately 0.021 inches. Preferably, the proximal section 18 of the deployment catheter 14 is formed of a nylon material having a durometer in the range of about 60D to 75D. The proximal section 18 of the deployment catheter 14 is sufficiently flexible to traverse a blood vessel, but is sufficiently rigid so that it may be passed through a blood vessel. The distal section 22 of the deployment catheter 14 is preferably formed of pellethane material having a durometer of between 25D and 55D, with a durometer of 40D being the preferred durometer.

The delivery system 12 includes a winged hub 24 coupled to the proximal section 18 of the deployment catheter 14. The winged hub 24 may be made from plastic and aids in the insertion of the deployment catheter 14 into a blood vessel. The delivery system 12 also includes an elongated core member 26. The core member 26 is a wire preferably made of nitinol, but may also be made from other metal alloys or a polymer material. The core member 26 is slideably disposed within the lumen 16 of the deployment catheter 14. The core member 26 may have a long taper or may have multiple tapers to give the proximal section 28 of the core member 26 a greater diameter than the distal section 30 of the core member 26. Preferably, the diameter of the proximal section 28 of the core member 26 is approximately 0.016 inches while the diameter of the distal section 30 of the core member 26 is about 0.002 inches. The greater diameter of the proximal section 28 of the core member 26 gives the core member 26 sufficient stiffness to be pushed through the deployment catheter 14 while the smaller diameter of the distal section 30 of the core member provides flexibility so that the core member 26 may traverse narrow blood vessels.

The delivery system 12 further includes a proximal cylindrical member 32 disposed about the distal section 30 of the core member 26. Preferably, the proximal cylindrical member 32 is a helically wound flexible coil with an outside diameter of about 0.016 inches. The coil may be made of a polymer material, but is preferably formed of metal. The delivery system 12 also includes an intermediate cylindrical member 34 disposed about the core member 26 distal of the proximal cylindrical member 32 and spaced apart from the proximal cylindrical member 32. The intermediate cylindrical member 34 takes the form of a cylindrical sleeve or a coil with an outside diameter of approximately 0.012 inches. The space between the proximal and intermediate cylindrical members 32 and 34 forms a first gap 36. The length of the first gap 36 ranges from 0.019 inches to 0.19 inches, with a preferred length of 0.040 inches.

The delivery system 12 further includes a distal cylindrical member 38 disposed about the core member 26 distal of the intermediate cylindrical member 34 and spaced apart from the intermediate cylindrical member 34. The distal cylindrical member 38 takes the form of a helically wound flexible coil having an outside diameter of about 0.016 inches. The coil may be formed from a polymer material, but is preferably formed from metal. The space between the intermediate and distal cylindrical members 34 and 38 forms a second gap 40. The length of the second gap 40 ranges from 0.019 inches to 0.19 inches, with a preferred length of 0.040 inches.

The delivery system 12 is described in more detail in U.S. patent applications Ser. Nos. 10/365,288 and 10/365,282, both entitled "Expandable Stent and Delivery System," (attorney Docket Nos. CRD1062-US-NP and CRD5001-US-NP) filed on Feb. 12, 2003, and assigned to the same assignee as the present patent application and hereby incorporated by reference.

The self-expanding stent 10 is mounted on the intermediate cylindrical member 34. The stent 10 includes longitudinal leg members, which extend from the proximal and distal ends 48, 50 of the stent 10. The stent 10 also includes anchor members 52a, 52b, 52c, and 52d, which take the form of radiopaque coils secured to the longitudinal leg members 44a, 44b, 46c, and 46d. The anchor members extend generally parallel to the longitudinal axis of the stent 10. The stent 10 is positioned and mounted on the intermediate cylindrical member 34 and the anchor members 52a, 52b at the proximal end 48 of the stent 10 align with and are positioned within the first gap 36. Similarly, the anchor members 52c, 52d at the distal end 50 of the stent 10 align with and are positioned within the second gap 40. In this configuration, the stent 10 is locked in place and may be advanced longitudinally through the deployment catheter 14.

Figure 2:
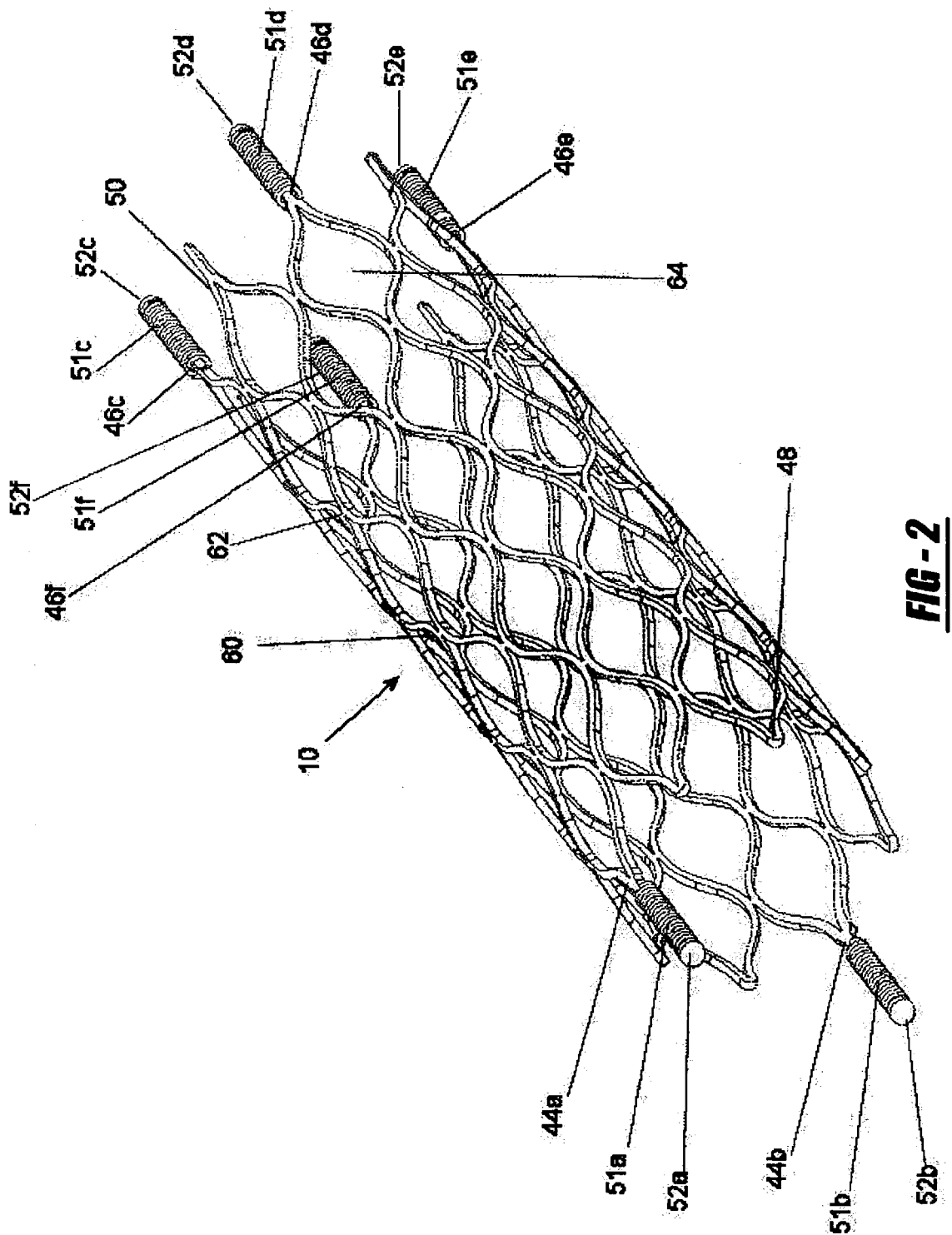
FIG. 2 is an oblique prospective view of the intravascular stent constructed in accordance with the preferred embodiment of the present invention.

FIG. 2 illustrates in more detail the stent 10, which is laser cut from a thin-walled nitinol tube to form a skeletal tubular member 60. The wall 62 of the tubular member 60 includes several openings, or cells 64. When the skeletal tubular member 60 is placed over an aneurysm, a physician is able to deliver embolic coils, or other such medical devices, through the cells 64 and into the aneurysm. The tubular member 60 holds, or retains, implanted medical devices, such as embolic coils, within the aneurysm. The tubular member 60 also functions as an aneurysm cover to cover the mouth of the aneurysm thus restricting, or partially restricting, the flow of blood into the aneurysm.

The length of the skeletal tubular member 60 is preferably in the range of 0.0795 inches to 3.15 inches. In an expanded state, the outer diameter of the skeletal tubular member 60 preferably extends up to about 0.4 inches. In a compressed state, the skeletal tubular member 60 is sized to fit within the lumen of the deployment catheter with a diameter on the order of about 0.012 inches.

Extending from the proximal end 48 of the stent 10 are two longitudinal proximal legs 44a, 44b. The proximal legs 44a, 44b generally extend parallel to the longitudinal axis of the stent 10. Coils 51a, 51b are disposed about the proximal legs 44a, 44b to form anchor members 52a, 52b. The coils 51a, 51b are helically wound coils and are preferably formed from a radiopaque material. The coils 51a, 51b are attached to the proximal legs 44a, 44b using a UV adhesive with a thermal cure cycle. The length of the coils 51a, 51b range from about 0.019 inches to 0.190 inches with a preferred length of about 0.040 inches.

Extending from the distal end 50 of the stent 10 are four longitudinal distal legs 46c, 46d, 46e and 46f. The distal leg members 46c, 46d, 46e and 46f extend generally parallel to the longitudinal axis of the stent 10. Coils 51c, 51d, 51e and 51f are disposed about the distal legs 46c, 46d, 46e and 46f, respectively, to form anchor members 52c, 52d, 52e and 52f, respectively. The coils 51c, 51d, 51e and 51f are also helically wound and formed from a radiopaque material and are attached to the distal legs 46c, 46d, 46e and 46f using a UV adhesive with a thermal cure cycle. The length of the coils 51*c*, 51*d*, 51*e* and 51*f* range from about 0.019 inches to 0.190 inches, with a preferred length of about 0.040 inches.

Figure 3:
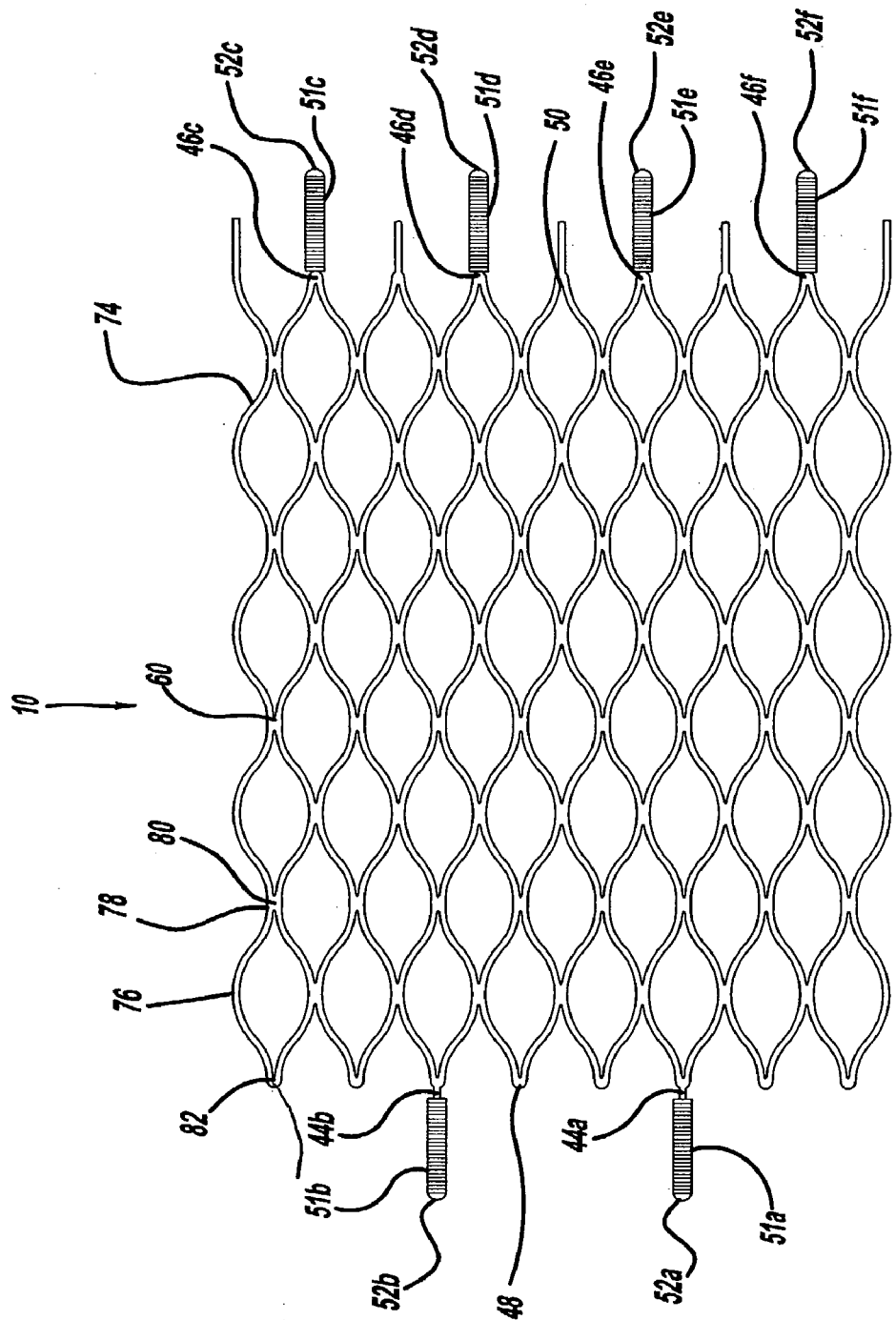
FIG. 3 is a side elevational view of the intravascular stent illustrated in FIG. 2 with the tubular stent being cut along a longitudinal line and flattened into a single plane; and, FIG. 4 is an enlarged sectional view of the intravascular stent deployed within a blood vessel.

FIG. 3 illustrates the repetitive cell pattern of the skeletal tubular member 60. This figure illustrates a side elevational view of the stent 10, with the stent cut along a longitudinal line and flattened into a single plane. Multiple sinusoidal members, such as the sinusoidal member 74, are interconnected to form the cell pattern of the stent. The sinusoidal members, such as the sinusoidal member 74, include a plurality of positive peaks, such as the positive peak 76, and negative peaks, such as the negative peak 78. The sinusoidal members are generally parallel to the longitudinal axis of the stent 10, and are generally parallel to each other. The positive peaks of each sinusoidal member are directly connected to the negative peaks of an adjacent sinusoidal member to form a connection point, such as the connection point 80.

The stent 10 includes a plurality of junctions, such as the junction 82, formed at both the distal end 50 and the proximal end 48 of the stent 10. Each junction is a point along the distal or proximal end 50, 48 where a positive peak of a sinusoidal member is directly connected to a negative peak of an adjacent sinusoidal member. The stent 10 includes eight of such junctions at the distal end 50 and eight of such junctions at the proximal end 48.

The stent 10 also includes a proximal leg 44*a*, which takes the form of a longitudinal projection extending from one of the junctions at the proximal end 48 of the stent 10. The stent 10 also includes a proximal leg 44*b*, which takes the form of a longitudinal projection extending from another junction at the proximal end 48 of the stent 10. Distal legs 46*c*, 46*d*, 46*e* and 46*f*, which take the form of longitudinal projections, extend from junctions at the distal end 50 of the stent 10. Radiopaque coils 51*a*, 51*b*, 51*c*, 51*d*, 51*e* and 51*f* are secured to each of the leg members 44*a*, 44*b*, 46*c*, 46*d*, 46*e* and 46*f* to form anchor members 52*a*, 52*b*, 52*c*, 52*d*, 52*e* and 52*f*.

The stent of the present invention may be coated with an agent, such as heparin or rapamycin, to prevent restenosis of the vessel. Examples of such coatings are disclosed in U.S. Pat. Nos. 5,288,711; 5,516,781; 5,563,146 and 5,646,160, the disclosures of which are incorporated herein by reference.

FIG. 4 illustrates the expandable stent 10 fully deployed within a blood vessel 90, and serving as an aneurysm cover to fully occlude the neck of an aneurysm 92. The deployment catheter 14 of the delivery system 12 has been moved proximally causing the anchor members 52*a*, 52*b*, 52*c*, 52*d*, 52*e* and 52*f* on the longitudinal leg members 44*a*, 44*b*, 46*c*, 46*d*, 46*e* and 46*f* on both the proximal end 48 and the distal end 50 of the stent 10 to exit the first gap 36 and the second gap 40 and thereby allow the stent 10 to become fully deployed. The first gap 36 is formed by the space between the proximal cylindrical member 32 and the intermediate cylindrical member 34. The second gap 40 is formed by the space between the intermediate cylindrical member 34 and the distal cylindrical member 38.

It should be appreciated that the stent 10 may also be resheathed during the deployment process. If during the expansion process, the anchor members 52*a*, 52*b* at the proximal end 48 of the stent 10 remain interlocked on the distal portion 30 of the core member 26, the stent 10 may be resheathed and deployed at a different location within the blood vessel 90. To resheath the stent 10, the deployment catheter 14 is moved distally, forcing the stent 10 back onto the intermediate cylindrical member 34 and forcing the anchor members 52*c*, 52*d*, 52*e* and 52*f* attached to the distal legs 46*c*, 46*d*, 46*e* and 46*f* at the distal end 50 of the stent to interlock within the second gap 40. Once resheathed, the stent 10 may be withdrawn or repositioned to a different location within the blood vessel 90.

Although a preferred embodiment of the invention has been described, it is to be understood that various modifications may be made by those skilled in the art without departing from the scope of the following claims.

That which is claimed is:

1. A self-expanding stent comprising:
   a small diameter skeletal tubular member having a thin wall and a longitudinal axis;
   said wall of said skeletal tubular member includes a plurality of cells which are formed by a plurality of interconnected sinusoidal members, said plurality of sinusoidal members are generally parallel to the longitudinal axis of said skeletal tubular member and in which no substantial portion of said sinusoidal members extends in a direction perpendicular to the longitudinal axis of said tubular member when the tubular member is expanded, said sinusoidal members are generally parallel to each other, and each of said plurality of sinusoidal members has a plurality of positive and negative peaks;
   the positive peaks of said sinusoidal members are connected to the negative peaks of adjacent sinusoidal members so as to form a repeating pattern of cells along the skeletal tubular member; and
   wherein a junction is formed at an end of the skeletal tubular member where a positive peak of one of said sinusoidal members is connected to a negative peak of an adjacent one of said sinusoidal members, a longitudinal leg member extends from said junction in a direction parallel to the longitudinal axis of the skeletal tubular member and said leg member terminates said connected sinusoidal members, and a helically wound coil is disposed about said longitudinal leg member.

2. A self-expanding stent as defined in claim 1, wherein a junction is formed at a distal end of the skeletal tubular member where a positive peak of one of said sinusoidal members is connected to a negative peak of an adjacent one of said sinusoidal members, a longitudinal leg member extends from said junction in a direction parallel to the longitudinal axis of the skeletal tubular member, and a helically wound coil is disposed about said longitudinal leg member.

3. A self-expanding stent as defined in claim 1, wherein a plurality of junctions are formed at a distal end of the skeletal tubular member where the positive peaks of the sinusoidal members are connected to the negative peaks of adjacent sinusoidal members, two longitudinal leg members each of which extend from one of said plurality of junctions, said longitudinal leg members extend in a direction parallel to the longitudinal axis of the skeletal tubular member, and a helically wound coil is disposed about each of said longitudinal leg members.

4. A self-expanding stent as defined in claim 1, wherein a plurality of junctions are formed at a distal end of the skeletal tubular member where the positive peaks of the sinusoidal members are connected to the negative peaks of adjacent sinusoidal members, four longitudinal leg members each of which extend from one of said plurality of junctions, said longitudinal leg members extend in a direction parallel to the longitudinal axis of the skeletal tubular member, and a helically wound coil is disposed about each of said longitudinal leg members.

5. A self-expanding stent as defined in claim 4, wherein each helically wound coil is formed of a radiopaque material.

6. A self-expanding stent as defined in claim 1, wherein a junction is formed at a proximal end of the skeletal tubular member where a positive peak of one of said sinusoidal members is connected to a negative peak of an adjacent one of said sinusoidal members, a longitudinal leg member extends from said junction in a direction parallel to the longitudinal axis of the skeletal tubular member, and a helically wound coil is disposed about said longitudinal leg member.

7. A self-expanding stent as defined in claim 1, wherein a plurality of junctions are formed at a proximal end of the skeletal tubular member where the positive peaks of the sinusoidal members are connected to the negative peaks of adjacent sinusoidal members, two longitudinal leg members extend from one of said plurality of junctions, said longitudinal leg members extending in a direction parallel to the longitudinal axis of the skeletal tubular member, and a helically wound coil is disposed about each of said longitudinal leg members.

8. A self-expanding stent as defined in claim 7, wherein each helically wound coil is formed of a radiopaque material.

9. A self-expanding stent as defined in claim 1, wherein said skeletal tubular member includes distal and proximal ends, and wherein a plurality of junctions are formed at both the distal and proximal ends of the skeletal tubular member where positive peaks of sinusoidal members are connected to negative peaks of adjacent sinusoidal members, a plurality of longitudinal leg members each extend from each of said plurality of junctions, said longitudinal leg members extending in a direction parallel to the longitudinal axis of the skeletal tubular member, and a helically wound coil is disposed about each of said longitudinal leg members.

10. A self-expanding stent as defined in claim 1, wherein said skeletal tubular member includes distal and proximal ends, and wherein a plurality of junctions are formed at both the distal and proximal ends of the skeletal tubular member where positive peaks of sinusoidal members are connected to negative peaks of adjacent sinusoidal members, four longitudinal leg members each extend from one of said plurality of junctions at the distal end of the skeletal tubular member and two longitudinal leg members each of which extend from one of said plurality of junctions at the proximal end of the skeletal tubular member, said longitudinal leg members extend in a direction parallel to the longitudinal axis of the skeletal tubular member, and a helically wound coil is disposed about each of said longitudinal leg members.

11. A self-expanding stent as defined in claim 10, wherein each helically wound coil is formed of a radiopaque material.

12. A self-expanding stent comprising:
a small diameter skeletal tubular member having distal and proximal ends, a thin wall and a longitudinal axis, said wall of said skeletal tubular member includes a plurality of cells which are formed by a plurality of interconnected sinusoidal members, said plurality of sinusoidal members are generally parallel to the longitudinal axis of said skeletal tubular member and in which no substantial portion of said sinusoidal members extends in a direction perpendicular to the longitudinal axis of said tubular member when the tubular member is expanded, said sinusoidal members are generally parallel to each other, and each of said plurality of sinusoidal members has a plurality of positive and negative peaks, said positive peaks of said sinusoidal members are directly connected to negative peaks of adjacent sinusoidal members so as to form a repeating pattern of cells along a length of said skeletal tubular member; and, a plurality of junctions are formed at both the distal and proximal ends of the skeletal tubular member where the positive peaks of the sinusoidal members are directly connected to the negative peaks of adjacent sinusoidal members, four longitudinal leg members each of which extend from one of said plurality of junctions at the distal end of the skeletal tubular member and from two longitudinal leg members each of which extend from one of said plurality of junctions at the proximal end of the skeletal tubular member, said leg members extending in a direction parallel to the longitudinal axis of the skeletal tubular member, and a helically wound radiopaque coil is disposed about each of said longitudinal leg members.

13. A self-expanding stent as defined in claim 12, wherein said cells permit the passage of embolic coils therethrough.

14. A self-expending stent comprising:
a small diameter thin-walled tubular member having a longitudinal axis;
said tubular member having cut-out portions to define a skeletal tubular member including a plurality of cells which are formed by a plurality of interconnected sinusoidal members, said plurality of sinusoidal members are generally parallel to the longitudinal axis of said skeletal tubular member and are generally parallel to each other, and each of said plurality of sinusoidal members has a plurality of positive and negative peaks;
the positive peaks of said sinusoidal members are connected to the negative peaks of adjacent sinusoidal members so to form a repeating pattern of cells along the skeletal tubular member; and
wherein a junction is formed at an end of the skeletal tubular member where a positive peak of one of said sinusoidal members is connected to a negative of an adjacent one of said sinusoidal members, a longitudinal leg member extends from said junction in a direction parallel to the longitudinal axis of the skeletal tubular member, and a helically wound coil is disposed about said longitudinal leg member.

15. A self-expanding stent as defined in claim 14, wherein a junction is formed at a distal end of the skeletal tubular member where a positive peak of one of said sinusoidal members is connected to a negative peak of an adjacent one of said sinusoidal members, a longitudinal leg member extends from said junction in a direction parallel to the longitudinal axis of the skeletal tubular member, and a helically wound coil is disposed about said longitudinal leg member.

16. A self-expanding stent as defined in claim 14, wherein a plurality of junctions are formed at a distal end of the skeletal tubular member where the positive peaks of the sinusoidal members are connected to the negative peaks of adjacent sinusoidal members, two longitudinal leg members each of which extend from one of said plurality of junctions, said longitudinal leg members extend in a direction parallel to the longitudinal axis of the skeletal tubular member, and a helically wound coil is disposed about each of said longitudinal leg members.

17. A self-expanding stent as defined in claim 14, wherein a plurality of junctions are formed at a distal end of the skeletal tubular member where the positive peaks of the sinusoidal members are connected to the negative peaks of adjacent sinusoidal members, four longitudinal leg members each of which extend from one of said plurality of junctions, said longitudinal leg members extend in a direction parallel to the longitudinal axis of the skeletal tubular member, and a helically wound coil is disposed about each of said longitudinal leg members.

18. A self-expanding stent as defined in claim 17, wherein each helically wound coil is formed of a radiopaque material.

19. A self-expanding stent as defined in claim 14, wherein a junction is formed at a proximal end of the skeletal tubular member where a positive peak of one of said sinusoidal members is connected to a negative peak of an adjacent one of said sinusoidal members, a longitudinal leg member extends from said junction in a direction parallel to the longitudinal axis of the skeletal tubular member, and a helically wound coil is disposed about said longitudinal leg member.

20. A self-expanding stent as defined in claim 14, wherein a plurality of junctions are formed at a proximal end of the skeletal tubular member where the positive peaks of the sinusoidal members are connected to the negative peaks of adjacent sinusoidal members, two longitudinal leg members extend from one of said plurality of junctions, said longitudinal leg members extending in a direction parallel to the longitudinal axis of the skeletal tubular member, and a helically wound coil is disposed about each of said longitudinal leg members.

21. A self-expanding stent as defined in claim 20, wherein each helically wound coil is formed of a radiopaque material.

22. A self-expanding stent as defined in claim 14, wherein said skeletal tubular member includes distal and proximal ends, and wherein a plurality of junctions are formed at both the distal and proximal ends of the skeletal tubular member where positive peaks of sinusoidal members are connected to negative peaks of adjacent sinusoidal members, a plurality of longitudinal leg members each extend from each of said plurality of junctions, said longitudinal leg members extending in a direction parallel to the longitudinal axis of the skeletal tubular member, and a helically wound coil is disposed about each of said longitudinal leg members.

23. A self-expanding stent as defined in claim 14, wherein said skeletal tubular member includes distal and proximal ends, and wherein a plurality of junctions are formed at both the distal and proximal ends of the skeletal tubular member where positive peaks of sinusoidal members are connected to negative peaks of adjacent sinusoidal members, four longitudinal leg membeis each extend from one of said plurality of junctions at the distal end of the skeletal tubular member and two longitudinal leg members each of which extend from one of said plurality of junctions at the proximal end of the skeletal tubular member, said longitudinal leg members extend in a direction parallel to the longitudinal axis of the skeletal tubular member, and a helically wound coil is disposed about each of said longitudinal leg members.

24. A self-expanding stent as defined in claim 23, wherein each helically wound coil is formed of a radiopaque material.

25. A self-expanding stent as defined in claim 1, wherein said cells permit the passage of embolic coils therethrough.

26. A self-expanding stent as defined in claim 14, wherein said cells permit the passage of embolic coils therethrough.

\* \* \* \* \*